United States Patent
Featherstone

(10) Patent No.: US 9,877,730 B2
(45) Date of Patent: Jan. 30, 2018

(54) NEPHROURETERECTOMY APPARATUS

(71) Applicant: Jonathan Featherstone, Pernarth (GB)

(72) Inventor: Jonathan Featherstone, Pernarth (GB)

(*) Notice: Subject to any disclaimer, the term of this patent is extended or adjusted under 35 U.S.C. 154(b) by 459 days.

(21) Appl. No.: 14/435,802

(22) PCT Filed: Oct. 11, 2013

(86) PCT No.: PCT/GB2013/052655
§ 371 (c)(1),
(2) Date: Apr. 15, 2015

(87) PCT Pub. No.: WO2014/060725
PCT Pub. Date: Apr. 24, 2014

(65) Prior Publication Data
US 2015/0250480 A1 Sep. 10, 2015

(30) Foreign Application Priority Data

Oct. 16, 2012 (GB) .................................. 1218575.7

(51) Int. Cl.
*A61M 29/00* (2006.01)
*A61B 17/12* (2006.01)
(Continued)

(52) U.S. Cl.
CPC .... *A61B 17/1219* (2013.01); *A61B 17/12099* (2013.01); *A61B 90/92* (2016.02);
(Continued)

(58) Field of Classification Search
CPC ............ A61M 17/12099; A61M 90/92; A61M 17/1219; A61M 2017/00893;
(Continued)

(56) References Cited

U.S. PATENT DOCUMENTS

| 4,798,193 A | 1/1989 | Giesy et al. |
| 2005/0095269 A1 | 5/2005 | Ainpour et al. |

(Continued)

FOREIGN PATENT DOCUMENTS

| CN | 202010361 U | 10/2011 |
| EP | 0547530 A1 | 6/1993 |

(Continued)

OTHER PUBLICATIONS

Search Report, dated Jan. 14, 2013, issued on Corresponding UK Patent Application No. GB1218575.7. 2 pages.
(Continued)

*Primary Examiner* — Eric Rosen
*Assistant Examiner* — Son Dang
(74) *Attorney, Agent, or Firm* — Kristjan Spence; Perry + Currier Inc.

(57) ABSTRACT

The apparatus includes a ureter occlusion apparatus, which comprises, in combination: at least one longitudinally extending plug body (26) of flexible, physiologically acceptable material which obstructs the passage of all particulate matter great than 5 microns in diameter, is laterally compressible to a compressed diameter of not more that 2 millimeters and is laterally expandable in the presence of liquid to an external diameter of at least 1.0 centimeter, a physiologically acceptable flexible guide sheath (21) dimensioned for removable insertion into the ureter, the guide sheath having an internal diameter for receiving the plug body in compressed dry form and being retractable around the plug body so as to leave the plug body in position in the ureter; and a removable physiologically acceptable stylet (22) and guide wire (20) which together allow positioning of the guide sheath within the ureter with both the guide wire and stylet being subsequently removable from the guide
(Continued)

sheath to allow the plug body to be installed in the ureter via the guide sheath.

4 Claims, 4 Drawing Sheets

(51) Int. Cl.
*A61B 90/92* (2016.01)
*A61B 17/00* (2006.01)
*A61B 90/00* (2016.01)

(52) U.S. Cl.
CPC .............. *A61B 2017/00893* (2013.01); *A61B 2017/00898* (2013.01); *A61B 2017/00902* (2013.01); *A61B 2017/1205* (2013.01); *A61B 2090/0807* (2016.02); *A61B 2090/3937* (2016.02); *A61B 2090/3966* (2016.02)

(58) Field of Classification Search
CPC .. A61M 2090/3966; A61M 2090/0807; A61M 2017/00902; A61M 2017/00898; A61M 2017/1205; A61M 2090/3937; A61M 25/0023; A61M 2025/0024; A61M 25/0097
See application file for complete search history.

(56) References Cited

U.S. PATENT DOCUMENTS

| | | |
|---|---|---|
| 2006/0058834 A1 | 3/2006 | Do et al. |
| 2007/0191768 A1* | 8/2007 | Kolb ................ A61B 17/12022 604/104 |
| 2011/0245841 A1* | 10/2011 | Shohat .................. A61B 17/22 606/127 |
| 2012/0203064 A1 | 8/2012 | Wynberg |

FOREIGN PATENT DOCUMENTS

| | | |
|---|---|---|
| EP | 2260768 A1 | 12/2010 |
| WO | WO 1980002369 A1 | 11/1980 |
| WO | WO 2004012587 A2 | 2/2004 |
| WO | WO 2009070686 A1 | 6/2009 |

OTHER PUBLICATIONS

Written Opinion of the International Searching Authority, dated Jan. 28, 2014, issued on Corresponding PCT International Patent Application No. PCT/GB2013/052655. 5 pages.

Second Office Action dated May 16, 2017, by SIPO, re Chinese Patent Application No. 201380053462.

Communication pursuant to Article 94(3) EPC (Examination Report) dated May 19, 2017, by EPO, re European Patent Application No. 13783358.

* cited by examiner

NEPHROURETERECTOMY APPARATUS

The present invention concerns apparatus for use in nephroureterectomy, and in particular ureteric occlusion apparatus for use in a nephroureterectomy procedure.

Nephroureterectomy is a standard surgical procedure in the case of upper urinary tract urothelial carcinoma (UUT-UC.). The procedure involves removal of the kidney and ureter (the conduit which drains urine from the kidney to the bladder) with excision of a bladder cuff at the distal end of the ureter (that is, the end remote from the kidney being surgically removed). Such a procedure may be carried out using either a traditional "open" surgical approach or, increasingly, by a laparoscopic ("keyhole") surgical approach.

During surgery, whether performed via an open or laparoscopic approach, there is a risk that cancer cells may be spilled or seeded into the bladder or into tissues adjacent the bladder during surgical mobilization and excision of the kidney and ureter (see, for example, Gkougkousis, E. G, Mellon J. K and Griffiths, T. R. L; Urol. Int. 2010; 85:249-256).

I have now devised apparatus which serves to alleviate the problem just identified.

According to the invention, therefore, there is provided a ureter occlusion apparatus, which comprises, in combination:

at least one longitudinally extending plug body of flexible, physiologically acceptable material which obstructs the passage of all particulate matter great than 5 microns in diameter being laterally compressible to a compressed diameter of not more that 2 millimeters and being laterally expandable in the presence of liquid to an external diameter of at least 1.0 centimeter, a physiologically acceptable flexible guide sheath dimensioned for removable insertion into the ureter, the guide sheath having an internal diameter for receiving the plug body in compressed dry form and being retractable around the plug body so as to leave the plug body in position in the ureter; and a removable physiologically acceptable stylet and guide wire, which together allow positioning of the guide sheath within the ureter with both the guide wire and stylet being subsequently removable from the guide sheath to allow the plug body to be installed in the ureter via the guide sheath.

The plug body typically comprises compressed foam of physiologically acceptable synthetic material; alternatively it may comprise compressed physiologically acceptable fibrous material provided that there are no pores (in the case of fibres, an inter-fibre spacing) of a maximum dimension exceeding 5 micrometers.

The plug body should, as previously indicated, be capable of swelling or expanding laterally (radially), but not longitudinally.

The plug body is preferably supplied in a sealed pack, in sterile, or sterilisable form. It is particularly preferred that the sealed pack contains the plug body in sterile form ready for use in a nephroureterectomy procedure.

By "physiologically acceptable", I mean free of ingredients which could interact in a deleterious manner with tissue in the course of a nephroureterectomy procedure. When physiologically acceptable ingredients are present in the plug body, they may further be selected to have beneficial effects, as will be explained below.

It is further preferred that the physiologically acceptable material of the plug body should be of non-flammable material, in order to permit part of the ureter (and the kidney to which it is attached) to be excised by a known technique such as electrocauterisation. Such electrocauterisation should leave the excised ureter attached to the kidney, but with the distal end of the ureter blocked by the plug body.

The plug body may, however, contain one or more pharmacologically active materials, such as cytotoxic agents, which may be provided in order to sterilize urothelial cells which might come into contact with the apparatus according to the invention during a nephroureterectomy procedure.

Examples of such cytotoxic agents include Mitomycin C and Epirubicin, which may be incorporated in the plug body so as to be slowly released in situ.

In one embodiment, the plug body in the apparatus according to the invention has pores of a maximum dimension of 5 micrometers. Such pores ensure that, in use, the plug body can permit drainage of urine longitudinally therethrough, thus enabling urine pressure between the kidney and the bladder to be dissipated. At the same time, such pores are of such size that they will block undesired passage of tumour particles, because the latter typically have a particle size of 10 to 20 micrometers.

The laterally expandable nature of the plug body permits it to expand (laterally) so as to block the ureter when the plug body is deployed into the ureter during surgery.

The specified unexpanded diameter (not more that 2 millimeters) permits the plug body to be dispensed into position using a longitudinally extending dispenser (or cannula), the plug body being provided in compressed form within the dispenser.

The plug body typically has an overall length of 5 to 6 centimeters, and it may include one or more circumferential markings or indicia to help guide insertion, as will be explained below. Such markings or indicia are preferably of a darker colour relative to the remainder of the plug body. The plug body may further comprise radiological marker material at its insertion end, such that the distance of insertion into the ureter can be monitored in use.

The plug body may comprise one or more surface formations ("spurs") arranged to hold the plug body in place, such as formations which taper outwardly towards the distal end (that is, towards the end of the ureter furthest from the kidney and therefore closest to the bladder and bladder cuff).

Such formations or spurs are typically shaped to engage with an internal wall of a distal part of the ureter to ensure that the plug body is held securely in place. The formations or spurs should be dimensioned such that they engage with the internal wall of the ureter, but without breaching or puncturing the latter.

In a further embodiment, the distal end (that is, the end remote from the kidney being surgically removed, as defined above) of the plug body may be of enlarged diameter to provide a stopper head which helps to avoid over-insertion into the ureter, in the manner of a stopper or bung. Such a head is preferably of a contrasting colour, to allow easy identification during deployment. Such a head can further fully cover the excised end of the ureter when that is excised together with the kidney, which also serves to visually confirm complete excision of the distal ureter to the operating surgeon.

Apart from the surface formations described, it is particularly preferred that the plug body is of substantially uniform cross-section along the length thereof.

In preferred embodiments, the plug body employed in ureter occlusion apparatus according to the invention has X-ray detectable material at one or both ends thereof.

The longitudinal surface of the plug body is preferably coloured blue, to provide good contrast with the colour of body tissue in which the apparatus is deployed.

The longitudinally extending flexible guide sheath acts as a tubular dispenser. Such a guide sheath is typically of physiologically acceptable plastics material, such as a polyether ether ketone (PEEK), and the guide sheath should have a smooth external surface along its entire length; the internal surface should also be smooth along the entire length thereof. The guide sheath is therefore preferably substantially cylindrical along all, or substantially all of its length. The guide sheath is furthermore preferably transparent along at least the majority of its length.

The guide sheath functions as a stent during dispensing, by supporting the inner wall of the ureter, and then permitting the plug to remain in place after the sheath has been withdrawn.

The at least one plug body is preferably provided in the guide sheath in a dry, unexpanded condition, such that the plug body can be dispensed into the ureter when the guide sheath is retracted over the plug body.

As indicated, the plug body used in apparatus according to the invention is deployed with a guide wire, the guide wire typically having a diameter of 0.3 to 0.4 millimeters.

In use, the guide sheath and stylet are preferably first positioned correctly in the ureter using a guide wire to advance the guide sheath to a desired position. Then the guide wire and stylet are then removed leaving the guide sheath in situ.

The apparatus preferably includes a guide tube applicator of similar internal diameter containing the plug body, the guide tube having an enlarged end with an internal diameter corresponding to the external diameter of the free end of the guide sheath, for smooth end to end docking engagement. The plug body can be inserted into the guide sheath after such end to end docking engagement.

The guide tube applicator is preferably of physiologically acceptable plastics material, such as a polyether ether ketone (PEEK), and the guide tube applicator preferably has an internal surface which is smooth along the entire length thereof.

It is further preferred that the apparatus according to the invention should include a plunger or pusher, which enables the plug body to be pushed from the docking guide tube applicator along the length of the guide sheath referred to above, to the desired position within the ureter.

The guide sheath is preferably made of clear plastic to allow visualization of plug insertion and may further have external marking (such as a black circumferential mark) to guide insertion.

Apparatus according to the invention may be used in a method of nephroureterectomy surgery, in which the plug body is inserted into the distal end of the ureter of a patient having upper urinary tract urothelial carcinoma using the guide sheath, the guide wire and the plunger of the nephroureterectomy apparatus as described above, the kidney and the majority of the ureter being excised as a unit, with the plug body occluding the distal end of the ureter. The kidney/ureter unit is then removed from the patient, the whole procedure preferably being carried out laparoscopically.

Preferred features of the invention will now be described, by way of example, in which.

Figure 1:
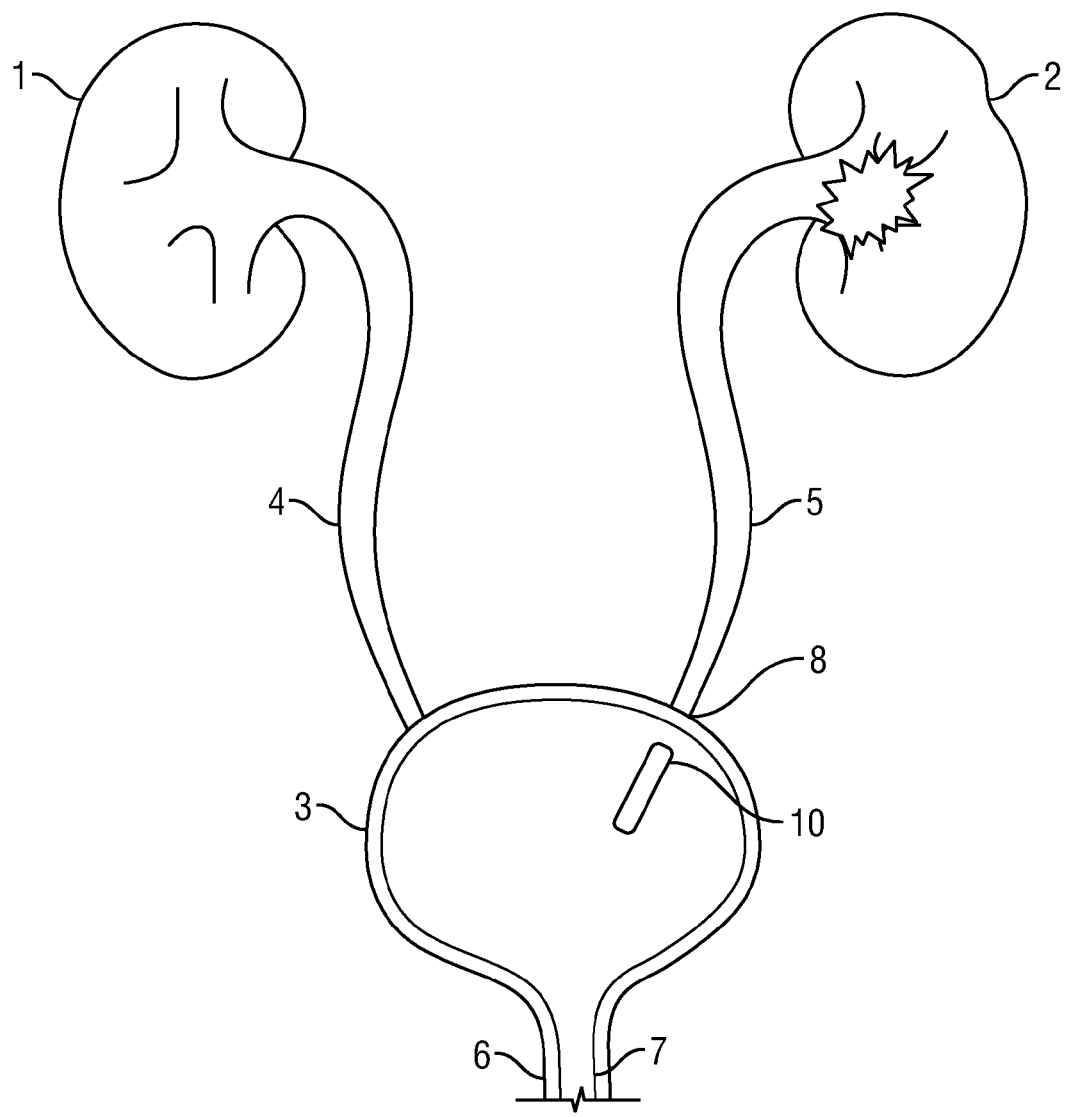
FIG. 1 is a schematic physiological drawing showing the interrelationship of the bladder, the ureter and the kidney, showing an exemplary plug body forming part of the occlusion apparatus according to the invention in situ.

As will be seen from FIG. 1, the human body generally includes a pair of kidneys 1,2, each of which is connected to the bladder 3 by a respective descending ureter 4,5. The bladder 3, which is a hollow elastic organ, sits on the pelvic floor (not shown). Urine enters the bladder 3 via the ureters 4,5 and exits past the sphincter 6 via the urethra 7.

Sometimes it is necessary to remove one of the kidneys in the case of upper urinary tract urothelial carcinoma: in this case the ureter is removed together with the kidney. There is, however, a risk that cancer cells may be spilled or seeded into the bladder or into tissues adjacent the bladder during surgical removal of a combination of kidney and ureter (2 and 5 in this case); thus according to the invention a longitudinally extending plug body 10 of flexible, physiologically acceptable material is placed at the inferior end 8 of the ureter 5 in order to provide an obstruction for the passage of all particulate matter greater than 5.0 micrometers in diameter; the plug body 10 is to be inserted into the ureter 5 using apparatus according to the invention, as will now be described in more detail with reference to FIG. 2 onwards.

Figure 2:
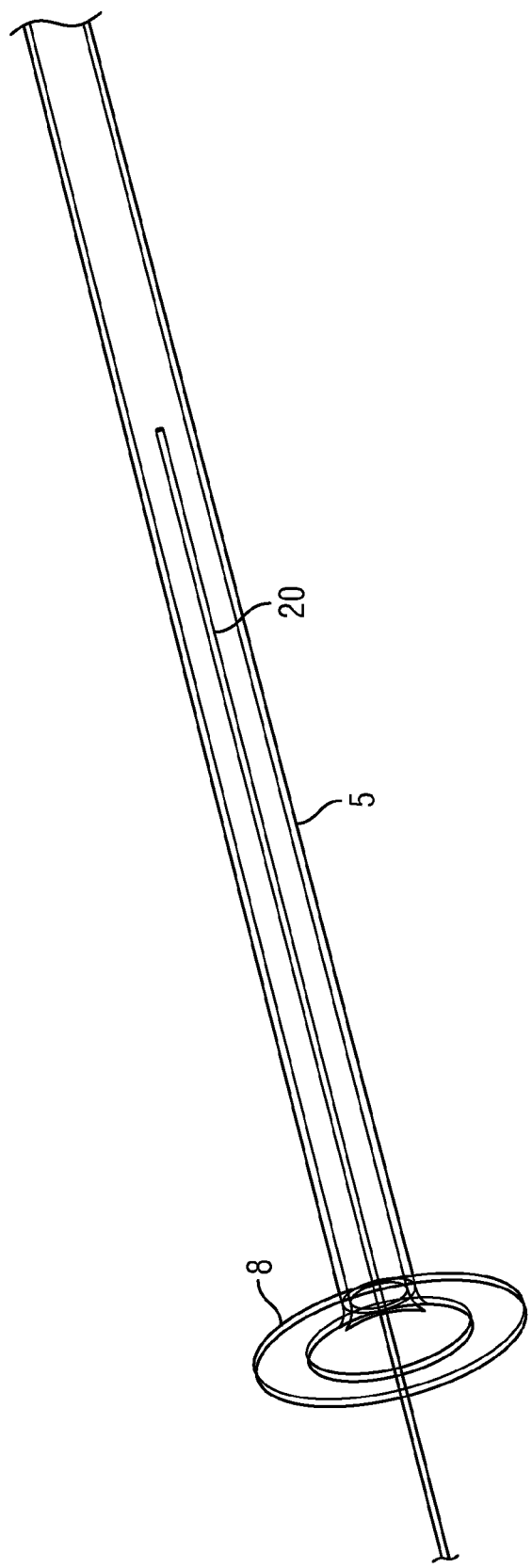
FIG. 2 is a schematic sectional drawing showing a first stage in the use of exemplary nephroureterectomy apparatus according to the invention when a guide wire is inserted into the ureter.

FIG. 2 schematically shows the ureter 5 into which is inserted, from the inferior (distal), or bladder, end 8, an elongate guide wire 20 (which is typically of stainless steel).

Figure 3:
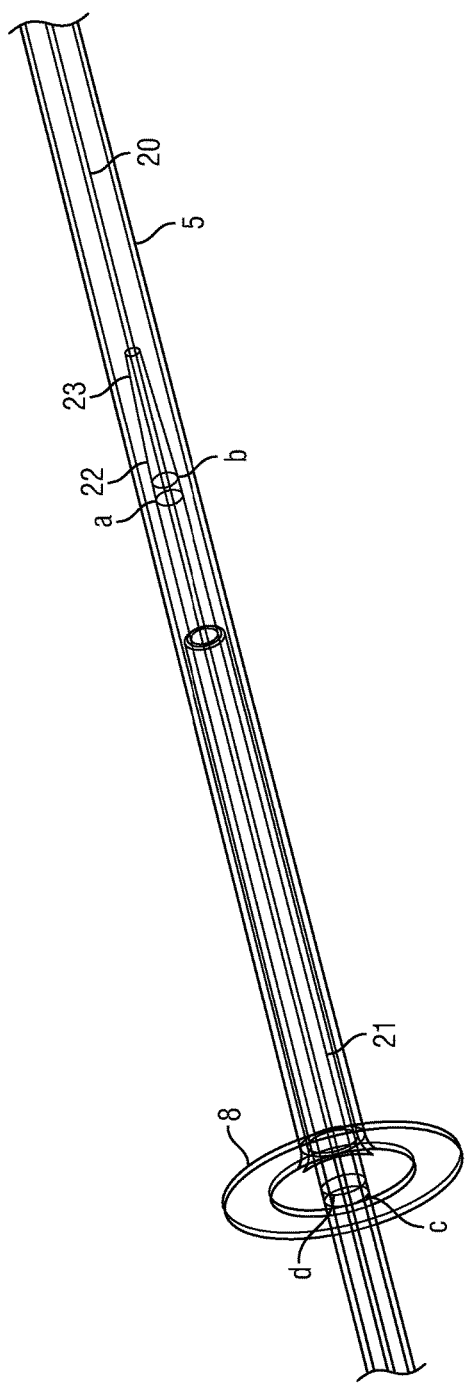
FIG. 3 is a similar sectional drawing showing a second stage in the use of the exemplary nephroureterectomy apparatus with a guide sheath and a stylet inserted into the ureter.

FIG. 3 then shows a guide sheath (or cannula) 21 which has been inserted along the length of the ureter, together with a stylet 22 having a tapered leading end 23 extending along the length of the guide sheath 21 and around the guide wire 20. The stylet 22 has a pair of circumferential marker lines a,b at the distal end of the stylet, at the transition between the tapered leading end 23 and the cylindrical body of the stylet 22, which body is such that the stylet can slide within the guide tube 21. The marker lines a, b are used for alignment of the stylet and hence the sheath tube 21. There are further circumferential marker lines c,d at the distal (or inferior) part of the guide sheath 21.

Figure 4:
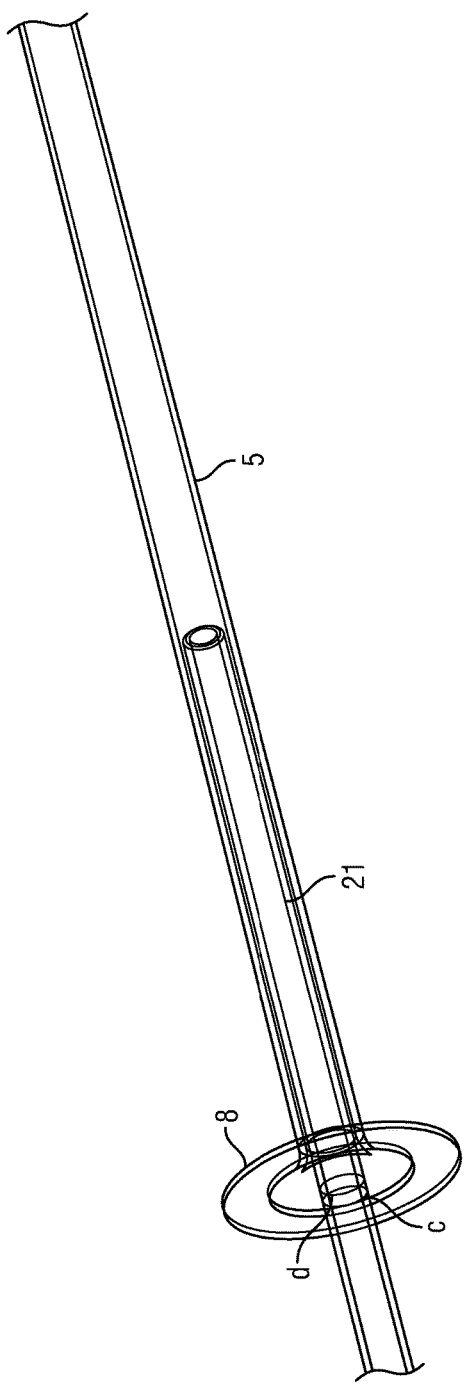
FIG. 4 is a similar sectional drawing showing a subsequent stage after withdrawal of the guide wire and stylet from the guide sheath.

First the guide wire 20 is removed along the length of the stylet 22, and then the stylet itself is removed, leaving the situation as shown in FIG. 4, in which just the guide sheath 21 remains in the ureter 5.

Figure 5:
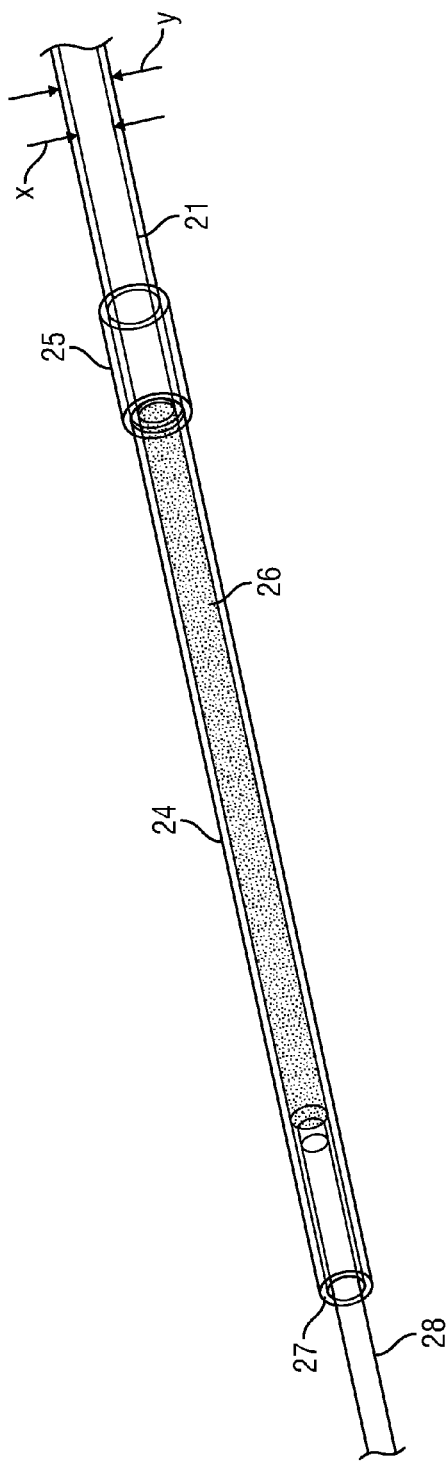
FIG. 5 is a similar sectional drawing showing the distal end of the guide sheath to which is docked a docking tube containing a longitudinally extending plug body.

Referring to FIG. 5, there is shown a guide tube 24 having an internal diameter "x" substantially the same as that of the sheath 21; the leading end of the guide tube 24 has an enlarged end portion 25 with an internal diameter "y" corresponding to the internal diameter of the sheath 21.

Wholly filling the lumen within the guide tube 24 is an expandable plug body 26 (corresponding to plug body 10 as shown in FIG. 1); in use, the plug body is pushed from the free end 27 of the guide tube 24 towards the enlarged end portion 25 and towards the part of the sheath 21 within the ureter, using a pusher or plunger 28. The pusher 28 is used to push the plug body 26 into the required location, marks on the pusher being provided to align with the marks on the sheath (the latter being preferably of clear plastics material such as the physiologically acceptable plastics materials described above).

Figure 6:
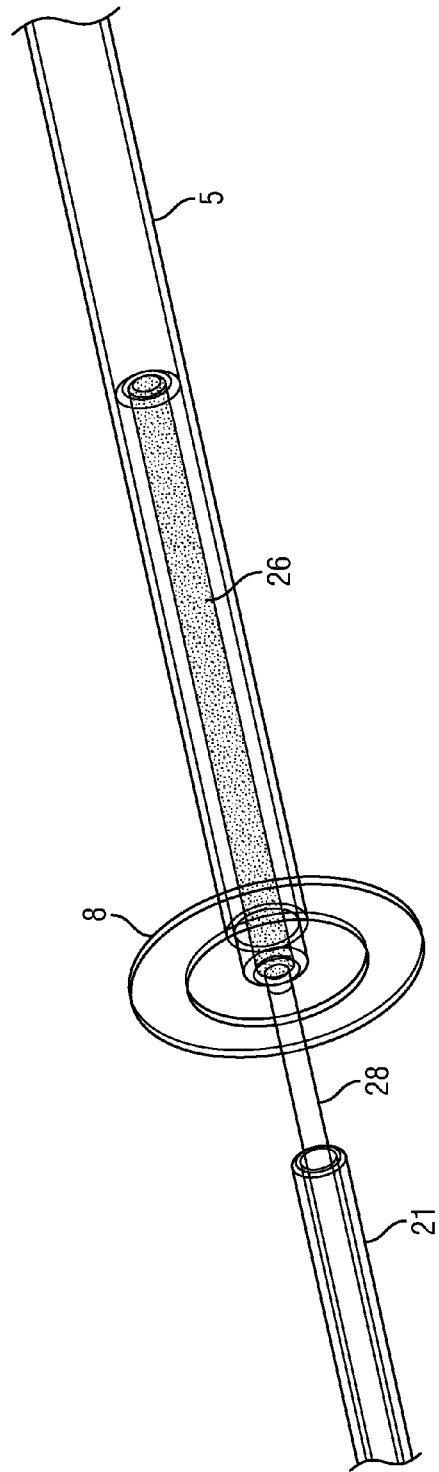
FIG. 6 is a similar sectional drawing showing withdrawal of the guide sheath to leave the plug body secure in the ureter.

The guide tube 24 is then removed (not shown) and then, as shown in FIG. 6, the sheath 21 is removed around the plug body 26, the latter being held in place by plunger 28, which is finally removed to leave the plug body in place at the distal end of the ureter 5.

What is claimed is:

1. A method of nephroureterectomy surgery, which comprises
    (a) providing:
        at least one longitudinally extending plug body of flexible, physiologically acceptable material which obstructs the passage of particulate matter greater than 5 microns in diameter, wherein the at least one plug body is laterally compressible to a compressed diameter of not more that 2 millimeters, and is laterally expandable in the presence of liquid to an external diameter of at least 1.0 centimeter;
        a physiologically acceptable flexible elongate guide sheath dimensioned for removable insertion into a patient's ureter, the guide sheath having an internal diameter for receiving the at least one plug body in compressed dry form and being retractable around the at least one plug body;
        a removable physiologically acceptable stylet; and
        a removable physiologically acceptable guide wire;
    (b) positioning said guide sheath in the ureter of a patient;
    (c) inserting the at least one plug body into the distal end of the ureter of a patient via said guide sheath by means of said stylet and said guide wire; and
    (d) removing said guide wire and said stylet from the ureter so as to leave the at least one plug body occluding the distal end of the ureter.

2. A method according to claim 1, in which the at least one plug body is pushed along the length of said guide sheath in step (c) by means of a plunger.

3. A method according to claim 1, in which the at least one plug body is introduced into said guide sheath in step (c) via a guide tube.

4. A method according to claim 3, wherein said guide tube has an enlarged end configured to dock with the outer diameter of an end of said guide sheath.

* * * * *